(12) United States Patent
Zaragoza Doerwald et al.

(10) Patent No.: US 9,126,915 B2
(45) Date of Patent: *Sep. 8, 2015

(54) METHOD FOR PREPARATION OF 2-(2,3-DIMETHYLPHENYL)-1-PROPANAL

(71) Applicant: LONZA LTD, Visp (CH)

(72) Inventors: Florencio Zaragoza Doerwald, Visp (CH); Anna Kulesza, Ausserberg (CH); Stephan Elzner, Brig-Glis (CH); Robert Bujok, Warsaw (PL); Zbigniew Wrobel, Warsaw (PL); Krzysztof Wojciechowski, Warsaw (PL)

(73) Assignee: Lonza Ltd., Visp (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/386,020

(22) PCT Filed: Nov. 15, 2012

(86) PCT No.: PCT/EP2012/072797
§ 371 (c)(1),
(2) Date: Sep. 18, 2014

(87) PCT Pub. No.: WO2013/011156
PCT Pub. Date: Jan. 24, 2013

(65) Prior Publication Data
US 2015/0080287 A1    Mar. 19, 2015

Related U.S. Application Data

(60) Provisional application No. 61/644,198, filed on May 8, 2012.

(30) Foreign Application Priority Data

May 8, 2012    (EP) .................................. 12167135
Oct. 5, 2012    (EP) .................................. 12187354
Oct. 22, 2012    (WO) ................. PCT/EP2012/070873
Nov. 14, 2012    (EP) .................................. 12192621

(51) Int. Cl.
*C07C 45/42* (2006.01)
*C07D 233/00* (2006.01)
*C07C 45/58* (2006.01)
*C07C 29/40* (2006.01)
*C07D 301/12* (2006.01)
*C07D 303/04* (2006.01)
*C11B 9/00* (2006.01)
*C07D 233/58* (2006.01)
*C07C 1/22* (2006.01)
*C07C 29/38* (2006.01)

(52) U.S. Cl.
CPC . *C07C 45/58* (2013.01); *C07C 1/22* (2013.01); *C07C 29/38* (2013.01); *C07C 29/40* (2013.01); *C07D 233/58* (2013.01); *C07D 301/12* (2013.01); *C07D 303/04* (2013.01); *C11B 9/0061* (2013.01)

(58) Field of Classification Search
CPC .............................. C07C 45/42; C07D 233/56
USPC .......................... 568/426; 548/346.1; 512/21
See application file for complete search history.

(56) References Cited

U.S. PATENT DOCUMENTS

| 4,514,412 | A | 4/1985 | Karjalainen et al. |
|---|---|---|---|
| 4,544,664 | A | 10/1985 | Karjalainen et al. |
| 4,621,150 | A | 11/1986 | Hirai et al. |
| 4,639,464 | A | 1/1987 | Karjalainen et al. |
| RE32,400 | E | 4/1987 | Karjalainen et al. |
| 4,826,864 | A | 5/1989 | Karjalainen et al. |
| 6,313,354 | B1 | 11/2001 | Markert et al. |
| 7,902,247 | B2 | 3/2011 | Sinha et al. |
| 7,902,377 | B2 | 3/2011 | Reine et al. |
| 8,735,438 | B2 | 5/2014 | Sinha et al. |
| 2009/0176843 | A1 | 7/2009 | Sinha et al. |
| 2010/0048915 | A1 | 2/2010 | Reine et al. |
| 2011/0077274 | A1 | 3/2011 | Sinha et al. |

FOREIGN PATENT DOCUMENTS

| AU | 4822172 | 5/1974 |
|---|---|---|
| DE | 2252080 | 5/1973 |
| EP | 0058047 | 8/1982 |
| EP | 0153692 | 9/1985 |
| EP | 1918282 | 5/2008 |
| GB | 2101114 | 1/1983 |
| GB | 2453982 | 4/2009 |
| JP | S51-100041 | 9/1976 |
| JP | S51-100042 | 9/1976 |
| NL | 7214315 | 5/1973 |
| WO | WO 98/45237 | 10/1998 |
| WO | WO 00/42851 | 7/2000 |
| WO | WO 2009/089132 | 7/2009 |
| WO | WO 2011/070069 | 6/2011 |

(Continued)

OTHER PUBLICATIONS

EP Application No. 12167135.8 Extended Search Report, Sep. 25, 2012.
PCT/EP2012/070870 International Search Report and Written Opinion, Feb. 1, 2013.
PCT/EP2012/072796 International Search Report and Written Opinion, Feb. 1, 2013.
PCT/EP2012/072796 Written Opinion, Jun. 17, 2014.

(Continued)

*Primary Examiner* — Sikarl Witherspoon
(74) *Attorney, Agent, or Firm* — Dority & Manning, P.A.

(57) ABSTRACT

The invention discloses a method for preparation of 2-(2,3-dimethylphenyl)-1-proponal from bromo 2,3-dimethyl-benzene and aceton, its use in perfumes and its use for the preparation of medetomidine.

9 Claims, No Drawings

(56) References Cited

FOREIGN PATENT DOCUMENTS

| WO | WO 2012/172120 | 12/2012 |
|----|----------------|---------|
| WO | WO 2013/011155 | 1/2013  |
| WO | WO 2013/011157 | 1/2013  |
| WO | WO 2013/011158 | 1/2013  |

OTHER PUBLICATIONS

PCT/EP2012/072796 International Preliminary Report on Patentability, Sep. 15, 2014.
PCT/EP2012/072797 Written Opinion, Feb. 1, 2013.
PCT/EP2012/072797 International Search Report, Feb. 1, 2013.
PCT/EP2012/072797 International Preliminary Report on Patentability, Apr. 25, 2014.
PCT/EP2012/072798 International Search Report and Written Opinion, Dec. 17, 2012.
PCT/EP2012/072799 International Search Report and Written Opinion, Mar. 20, 2013.
Cordi et al., Efficient Synthesis of (S)-4(5)-[1-2,3-Dimethylphenyl) ethyl] Imidazole Tartrate, the Potent $\alpha_2$ Adrenoreceptor Agonist Dexmedetomidine, Synthetic Communications, 26(8), pp. 1585-1593 (1996).
Huebner et al., Aconite alkaloids, XVI. Staphisine and the hydrocarbon obtained from its dehydrogenation, Journal of Biological Chemistry, vol. 169, pp. 211-220, (1947).
Mukherjee-Muller et al., 176. Säurekatalysierte Umlagerungen von 1,5.Dimethyl-6-methyliden-tricyclo[3.2.1.0 2,7]oct-3-en-8endoglen, Helvetica Chimica Acta, vol. 60, Fasc. 5, pp. 1758-1780, (1977).
Zhang et al., Ultrasound-Promoted Synthesis of Substituted Phenanthrene-1,4-Quinones : The Structure of Plectranthon D, Tetrahedron Letters, vol. 23, No. 14, pp. 2153-2156, (1994).

METHOD FOR PREPARATION OF 2-(2,3-DIMETHYLPHENYL)-1-PROPANAL

RELATED APPLICATIONS

This application is the national stage entry of International Patent Application No. PCT/EP2012/072797 having a filing date of Nov. 15, 2012, which claims the filing benefit of European Patent Application No. 12192621.6, having a filing date of Nov. 14, 2012, International Patent Application No. PCT/EP2012/070873, having a filing date of Oct. 22, 2012, European Patent Application No. 12187354.1, having a filing date of Oct. 5, 2012, U.S. Provisional Application No. 61/644,198, having a filing date of May 8, 2012, and European Patent Application No. 12167135.8, having a filing date of May 8, 2012, all of which are incorporated herein by reference in their entirety.

The invention discloses a method for preparation of 2-(2, 3-dimethylphenyl)-1-propanal from 1-bromo 2,3-dimethylbenzene and aceton, its use in perfumes and its use for the preparation of medetomidine.

Aromatic aldehydes are widely used as flavours and fragrances in cosmetics, perfumes, and numerous household products. Alpha, beta-unsaturated aromatic aldehydes, such as substituted cinnamic aldehydes, are known to have distinct fragrance and are therefore used in the perfume industry WO 98/45237 A discloses certain aromatic aldehydes, a method for producing them starting from acetophenone acetals, their use as perfumes and their use as intermediates for the preparation of 3-arylpropanals. They have a musky fragrance.

Mukherjee-Müller et al., Helvetica Chimica Acta, 1977, 60, 1758-1780, discloses a process for the preparation of 2-(dimethylphenyl) propanaldehydes as a mixture of 3 unidentified isomers. The position of the methyl on the aromatic groups is unknown. These compounds are prepared by a rearrangement reaction in the presence of an acidic catalyst (sulfuric acid) from certain tricyclic alcohols.

The perfume and household product industry has a constant need for new perfumes with interesting, new and not yet available fragrances in order to increase the available choice of fragrances and to adapt the fragrances to the ever changing demand of fashion. Furthermore the respective substances need to be synthesized economically and with consistent quality. High purity and strong fragrances are desired. The present invention provides a new alpha, beta-unsaturated aromatic aldehyde, which has strong and interesting, aldehydic fragrance, intensely spicy and sweet, and an improved process for the production thereof.

In the following text,
halogen means F, Cl, Br or I, preferably Cl, Br or I;
"alkyl" means linear, branched, cyclic or cyclo alkyl, preferably it means the commonly accepted meaning linear or branched alkyl; if not otherwise stated. Examples of "alkyl" include methyl, ethyl n-propyl, isopropyl, n-butyl, sec-butyl, tert-butyl, pentyl, hexyl, heptyl, cyclopropyl, cyclobutyl, cyclopentyl, cyclohexyl, cycloheptyl, norbornyl, adamantyl, and the like;
"cyclic alkyl" or "cyclo alkyl" are intended to include cyclo aliphatic, bicyclo aliphatic and tricycle aliphatic residues;
"alkane" means a linear, branched or cyclic alkane, preferably linear or branched alkane;
"alkanol" means a hydroxyalkane, with alkane having the meaning as defined above also with its preferred embodiments;
Ac acetyl;
tBu tertiary butyl;
DBU 1,8-diazabicyclo[5.4.0]undec-7-ene;
DABCO 1,4-diazabicyclo[2.2.2]octane;
DIPEA N-ethyl-N,N-diisopropylamine;
DMA N,N-dimethylacetamide;
DMF N,N-dimethylformamide;
EDTA-$Na_2$ ethylene diamine tetraacetic acid disodium;
hexanes mixture of isomeric hexanes;
NMP N-methyl-2-pyrrolidone;
OTf trifluoromethanesulfonate, also known as triflate;
MPS $KHSO_5$, also known as potassium peroxymonosulfate or potassium monopersulfate, and marketed as a triple salt with the formula 2 $KHSO_5$ $KHSO_4$ $K_2SO_4$ under the trade names Caroat® and Oxone®, therefore $KHSO_5$ is often used in form of this triple salt;
salen ligand obtained from a condensation of salicylaldehyde or of a substituted salicylaldehyde derivative with ethylene diamine or with a substituted ethylene diamine;
sulfamic acid HO—$SO_2$—$NH_2$;
TEMPO 2,2,6,6-tetramethylpiperidine 1-oxyl;
THF tetrahydrofuran;
xylene 1,2-dimethylbenzene, 1,3-dimethylbenzene, 1,4-dimethylbenzene or a mixture thereof;
if not otherwise stated.

Subject of the invention is a method for preparation of compound of formula (XXI);

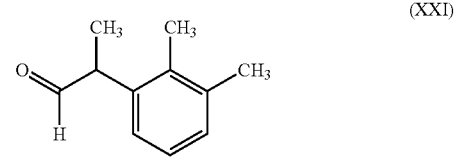

the method comprises a step (N);
step (N) comprises a reaction (N-reac);
reaction (N-reac) is a reaction of compound of formula (XXII) with a catalyst (N-cat);

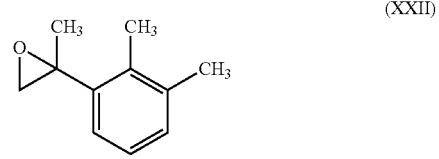

catalyst (N-cat) is selected from the group consisting of acetic acid, formic acid, trifluoroacetic acid, methanesulfonic acid, benzenesulfonic acid, p-toluenesulfonic acid, camphorsulfonic acid, HCl, HBr, $H_2SO_4$, $HNO_3$, $H_3PO_4$, $HClO_4$, $BCl_3$, $BBr_3$, $BF_3OEt_2$, $BF_3SMe_2$, $BF_3THF$, $MgCl_2$, $MgBr_2$, $MgI_2$, $AlCl_3$, Al(O—$C_{1-4}$ alkyl)$_3$, $SnCl_4$, $TiCl_4$, Ti(O—$C_{1-4}$ alkyl)$_4$, $ZrCl_4$, $Bi_2O_3$, $BiCl_3$, $ZnCl_2$, $PbCl_2$, $FeCl_3$, $ScCl_3$, $NiCl_2$, Yb(OTf)$_3$, Yb(Cl)$_3$, $GaCl_3$, $AlBr_3$, Ce(OTf)$_3$, LiCl, Cu(BF$_4$)$_2$, Cu(OTf)$_2$, NiBr$_2$(PPb$_3$)$_2$, $NiBr_2$, $NiCl_2$, Pd(OAc)$_2$, $PdCl_2$, $PtCl_3$, $InCl_3$, acidic inorganic solid substance, acidic ion exchange resin, carbon treated with inorganic acid and mixtures thereof.

Preferably, the acidic inorganic solid substance is aluminosilicates.

Preferably, the acidic ion exchange resin is selected from the group consisting of copolymers of styrene and divinylbenzene and of perfluorinated branched or linear polyethylenes, these polymers being functionalized with $SO_3H$ groups;

more preferably, the acidic ion exchange resin is selected from the group consisting of copolymers of styrene and divinylbenzene containing more than 5% of divinylbenzene, preferably being macroreticular, and of perfluorinated polyethylenes, these polymers being functionalized with $SO_3H$ groups.

Preferably, the inorganic acid, with which the carbon was treated, is selected from the group consisting of HCl, $H_2SO_4$ and $HNO_3$.

Preferably, the catalyst (N-cat) is selected from the group consisting of acetic acid, formic acid, trifluoroacetic acid, methanesulfonic acid, p-toluenesulfonic acid, HCl, HBr, $H_2SO_4$, $H_3PO_4$, $BCl_3$, $BF_3OEt_2$, $MgCl_2$, $MgBr_2$, $AlCl_3$, $ZnCl_2$, $Cu(BF_4)_2$, aluminosilicates, acidic ion exchange resins, carbon treated with HCl, $H_2SO_4$ or $HNO_3$, and mixtures thereof;

more preferably, the catalyst (N-cat) is selected from the group consisting of acetic acid, formic acid, methanesulfonic acid, p-toluenesulfonic acid, HCl, $H_2SO_4$, $BF_3OEt_2$, Cu $(BF_4)_2$, aluminosilicates, acidic ion exchange resins, and mixtures thereof.

Preferably, reaction (N-reac) is done in a solvent (N-solv);
solvent (N-solv) is selected from the group consisting of water, tert-butanol, isopropanol, acetonitrile, propionitrile, THF, methyl-THF, NMP, dioxane, 1,2-dimethoxyethane, dichloromethane, 1,2-dichloroethane, chloroform, toluene, benzene, chlorobenzene, hexane, cyclohexane, ethyl acetate, acetic acid, formic acid, trifluoroacetic acid and mixtures thereof;

preferably from water, acetonitrile, propionitrile, THF, 2-methyl-THF, 1,2-dimethoxyethane, dichloromethane, 1,2-dichloroethane, chloroform, toluene, cyclohexane, ethyl acetate, acetic acid, formic acid and mixtures thereof;

more preferably from water, acetonitrile, propionitrile, THF, 2-methyl-THF, 1,2-dimethoxyethane, dichloromethane, 1,2-dichloroethane, toluene, ethyl acetate and mixtures thereof;

even more preferably from acetonitrile, THF, 2-methyl-THF, dichloromethane, toluene, ethyl acetate and mixtures thereof.

The catalyst (N-cat) can be used in a pure form or as hydrate.

The catalyst (N-cat) can be used as a solution in solvent (N-solv).

Preferably, the molar ratio between catalyst (N-cat) and compound of formula (XXII) is from 1:1000 to 10:1, more preferably from 1:100 to 5:1, even more preferably from 1:20 to 1:1, especially from 1:10 to 1:2.

Preferably, the reaction temperature of reaction (N-reac) is from −20 to 200° C., more preferably from 0 to 150° C., even more preferably from 10 to 100° C.

The reaction (N-reac) can be done in a system, that is closed or open to the atmosphere. In a closed system, the pressure depends mainly on the boiling point of a solvent (N-solv) and on the reaction temperature of reaction (N-reac).

Preferably, the reaction (N-reac) is done at a pressure of from 0.01 bar to 20 bar, more preferably of from 0.1 to 10 bar, even more preferably of from atmospheric pressure to 5 bar. More preferably, the reaction (N-reac) is done in an open system.

Preferably, the reaction time of reaction (N-reac) is from 30 min to 72 h, more preferably from 1 h to 48 h, even more preferably from 2 h to 24 h.

Alternatively, reaction (N-reac) can be done as a continuous gas-phase reaction by passing the evaporated compound of formula (XXII) over the catalyst (N-cat). This gas-phase reaction can be done in the presence of an inert, gas, the inert gas is preferably selected from the group consisting of nitrogen, a noble gas and carbon dioxide.

After reaction (N-reac), compound of formula (XXI) can be isolated by standard methods such as evaporation of volatile components, extraction, washing, drying, concentration, filtration, crystallization, distillation, chromatography and any combination thereof, which are known per se to the person skilled in the art.

Preferably, any volatile components of the reaction mixture or added or generated during work up can be removed by evaporation under reduced pressure.

Preferably, the reaction mixture resulting from reaction (N-reac) or any aqueous phase during the work up after reaction (N-reac) can be extracted with a solvent (M-extract), solvent (M-extract) is preferably selected from the group consisting of water, toluene, benzene, xylene, chlorobenzene, dichloromethane, chloroform, acetic acid $C_{1-8}$ alkyl ester and combinations thereof;

the acetic acid $C_{1-8}$ alkyl ester is preferably an acetic acid $C_{1-4}$ alkyl ester, more preferably selected from the group consisting of ethyl acetate, isopropyl acetate and butyl acetate; preferably solvent (M-extract) is selected from the group consisting of toluene, dichloromethane, ethyl acetate, isopropyl acetate and mixtures thereof.

Preferably, any washing of any organic phase after reaction (N-reac) can be done with water, with a base (M-basify), with an aqueous solution of a base (M-basify), with an aqueous solution of an acid (M-acid) or with brine.

Preferably base (M-basify) is selected from the group consisting of $NaHCO_3$, $Na_2CO_3$, NaOH and mixtures thereof.

Preferably, base (M-basify) is added in such an amount, that the pH of the resulting mixture is from 7 to 12, more preferably from 8 to 10, even more preferably from 8 to 9.

Preferably, acid (M-acid) is selected from the group consisting of oxalic acid, citric acid, maleic acid, fumaric acid, tartaric acid, $NH_4Cl$, HCl, HBr, $H_2SO_4$, $H_3PO_4$ and mixtures thereof.

Any extraction or washing can be followed by filtration and concentration of the extract or of the washed mixture.

In another preferred embodiment, compound of formula (XXI) is purified after reaction (N-reac) by chromatography.

Any organic phase can be dried, preferably over $MgSO_4$ or $Na_2SO_4$.

Any concentration is preferably done by distillation, preferably under reduced pressure.

Compound of formula (XXI) can be obtained in step (N) as the aldehyde as depicted in formula (XXI), but also in form of its hydrate or hemiacetal. The hemiacetal of compound of formula (XXI), which can result as product from step (N), can be the product of an addition reaction between the aldehyde as depicted in formula (XXI) and an alcohol selected from the group consisting of tert-butanol and isopropanol, or between the aldehyde as depicted in formula (XXI) and any alcohol which is used during the isolation after reaction (N-reac).

Therefore formula (XXI) for the purpose of this invention encompasses the aldehyde, hydrate and the hemiacetal.

When compound of formula (XXI) is obtained from reaction (N-reac) in form of its hydrate or of a hemiacetal, the hydrate or the hemiacetal can be converted into the aldehyde by standard reactions known to the person skilled in the art.

Preferably, compound of formula (XXII) is prepared in a step (O) or in two steps, the two steps are step (O1) and step (O2);
step (O) comprises a reaction (O-reac);
reaction (O-reac) is a reaction of compound of formula (XXIII), with a reagent (O-reag);

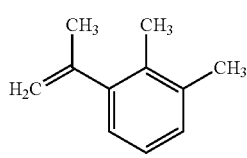

(XXIII)

reagent (O-reag) is selected from the group consisting of peracetic acid, trifluoroperacetic acid, perbenzoic acid, 3-chloroperbenzoic acid, raonoperphthalic acid, dimethyldioxirane, tert-butylhydroperoxide, dibenzoyl peroxide, cumenehydroperoxide, oxygen, air, sodium hypochlorite, $KHSO_5$, $Na_2O_2$, aqueous $H_2O_2$, $H_2O_2$ dissolved in acetic acid, $H_2O_2$ dissolved in trifluoroacetic acid, and mixtures thereof;

step (O1) comprises a reaction (O1-reac);

reaction (O1-reac) is a reaction of compound of formula (XXIII) with water and with a compound (O1-comp);

compound (O1-comp) is selected from the group consisting of bromine, N-bromosuccinimide, chlorine, N-chlorosuccinimide, iodine, N-iodosuccinimide, IBr, BrCl, and mixtures thereof;

step (O2) comprises a reaction (O2-reac);

reaction (O2-reac) is a reaction of the reaction product from reaction (O1-reac) with a base (O2-base);

base (O2-base) is selected from the group consisting of sodium hydroxide, potassium hydroxide, calcium hydroxide and mixture thereof.

Preferably, reagent (O-reag) is selected from the group consisting of peracetic acid, tert-butylhydroperoxide, oxygen, air, sodium hypochlorite, aqueous $H_2O_2$, $H_2O_2$ dissolved in acetic acid, $H_2O_2$ dissolved in trifluoroacetic acid, and mixtures thereof;

more preferably, reagent (O-reag) is aqueous $H_2O_2$.

Preferably, reaction (O-reac) is done in a solvent (O-solv);

solvent (O-solv) is selected from the group consisting of water, aqueous solutions of $NaHCO_3$, $Na_2CO_3$, $(NH_4)HCO_3$, $(NH_4)_2CO_3$, $KHCO_3$ or $K_2CO_3$, benzene, toluene, NMP, dioxane, acetone, ethyl acetate, methylethylketone, tert-butanol, acetonitrile, chloroform, dichloromethane and mixtures thereof;

preferably from water, aqueous solutions of $NaHCO_3$, $Na_2CO_3$, $KHCO_3$ or $K_2CO_3$, toluene, dioxane, acetone, ethyl acetate, methylethylketone, tert-butanol, acetonitrile, dichloromethane and mixtures thereof.

Reaction (O-reac) can be done in the presence of a catalyst (O-cat);

catalyst (O-cat) is selected from the group consisting of trifluoroacetic acid, trifluoroacetone, Mn(salen) complex, aldehydes, N-methylmorpholine N-oxide, 2,2,6,6-tetramethylpiperidine 1-oxyl and mixtures thereof;

aldehydes are preferably isobutyraldehyde or benzaldehyde.

Reaction (O-reac) can be done in the presence of a buffer (O-buff); preferably, buffer (O-buff) is an aqueous buffer and is selected from the group consisting of $K_2CO_3$/EDTA-$Na_2$ buffer, phosphate buffer and other buffers known by the skilled person; more preferably, buffer (O-buff) is an $K_2CO_3$/EDTA-$Na_2$ buffer.

Preferably, the reaction temperature of reaction (O-reac) is from −20 to 100° C., more preferably from −10 to 80° C., even more preferably from 0 to 50° C.

The reaction (O-reac) can be done in a system, that is closed or open to the atmosphere.

In a closed system, the pressure depends on the boiling point of a solvent (O-solv) and on the reaction temperature of reaction (O-reac).

Preferably, the reaction (N-reac) is done at a pressure of from 0.01 bar to 20 bar, more preferably of from 0.1 to 10 bar, even more preferably of from atmospheric pressure to 5 bar. More preferably the reaction (O-reac) is done in an open system.

Preferably, the reaction time of reaction (O-reac) is from 30 mm to 72 h, more preferably from 1 h to 48 h, even more preferably from 2 h to 24 h.

After the reaction (O-reac), the compound of formula (XXII) cart be isolated by standard methods such as evaporation of volatile components, extraction, washing, drying, concentration, crystallization, distillation, chromatography and any combination thereof.

Preferably, reaction (O1-reac) and reaction (O2-reac) are conducted in solvent (O-solv), with solvent (O-solv) as defined above, also with all its preferred embodiments.

Preferably, the reaction temperatures of reaction (O1-reac) and of reaction (O2-reac) are identical or different and independently from each other from −20 to 100° C., more preferably from −10 to 80° C., even more preferably from 0 to 50° C.

Reaction (O1-reac) and reaction (O2-reac) can independently from each other be done in systems, that are closed or open to the atmosphere.

In a closed system, the pressure depends on the boiling point of a solvent (O-solv) and on the reaction temperature of reaction (O1-reac) and reaction (O-reac) respectively.

Preferably, reaction (O1-reac) and reaction (O2-reac) are Independently from each other done at pressures of from 0.01 bar to 20 bar, more preferably of from 0.1 to 10 bar, even more preferably of from atmospheric pressure to 5 bar.

More preferably, reaction (O1-reac) and reaction (O2-reac) are done in a open system.

Preferably, the reaction times of reaction (O1-reac) and of reaction (O2-reac) are independently from each other from 30 min to 72 h, more preferably from 1 h to 48 h, even more preferably from 2 h to 24 h.

The reaction product of reaction (O1-reac) and the compound of formula (XXII) from reaction (O2-reac) can be isolated by standard methods such as evaporation of volatile components, extraction, washing, drying, concentration, filtration, crystallization, distillation, chromatography and any combination thereof.

Reaction (O1-reac) and reaction (O2-reac) can be done consecutively without isolation of the reaction product of reaction (O1-reac), they can be done in one pot.

Preferably, compound of formula (XXII) is not isolated, step (N) is done directly after step (O) or step (O2) respectively in one pot. For this, catalyst (N-cat) is simply added to the reaction mixture resulting from reaction (O-reac) or from reaction (O2-reac) respectively.

Preferably, compound of formula (XXIII) is prepared in a step (P);

step (P) comprises a reaction (P-reac);

in reaction (P-reac) the compound of formula (XXIV) is exposed to a temperature (P-temp);

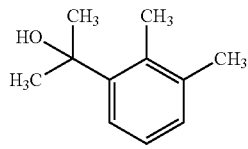

(XXIV)

temperature (P-temp) is from 0 to 300° C.

Preferably, temperature (P-temp) is from 5 to 200° C., more preferably from 100 to 150° C.

Reaction (P-reac) can be done in a solvent (P-solv);

solvent (P-solv) is selected from the group consisting of benzene, toluene, xylene, hexane, heptane, 1,2-dichloroethane, NMP, dichloromethane, chloroform and mixtures thereof;

preferably from benzene, toluene, xylene, dichloromethane and mixtures thereof.

Preferably, reaction (P-reac) is done in the presence of a catalyst (P-cat);

catalyst (P-cat) is selected from the group consisting of acetic acid, formic acid, trifluoroacetic acid, methanesulfonic acid, benzenesulfonic acid, p-toluenesulfonic acid, camphorsulfonic acid, HCl, HBr, $H_2SO_4$, KOH, NaOH, $KHSO_4$, $HNO_3$, $H_3PO_4$, $HClO_4$, $BCl_3$, $BBr_3$, $BF_3OEt_2$, $BF_3SMe_2$, $BF_3THF$, $MgCl_2$, $MgBr_2$, $MgI_2$, $AlCl_3$, $Al(O-C_{1-4}\ alkyl)_3$, $I_2$, $Al_2O_3$, $SnCl_4$, $TiCl_4$; $Ti(O-C_{1-4}\ alkyl)_4$, $ZrCl_4$, $Bi_2O_3$, $BiCl_3$, $ZnCl_2$, $PbCl_2$, $FeCl_3$, $Yb(OTf)_3$, $Yb(Cl)_3$, $GaCl_3$, $AlBr_3$, $Ce(OTf)_3$, LiCl, acidic insoluble inorganic solid, acidic ion exchange resins, carbon treated with an inorganic acid, and mixtures thereof;

preferably from methanesulfonic acid, benzenesulfonic acid, p-toluenesulfonic acid, $H_2SO_4$, $KHSO_4$, $H_3PO_4$, acidic insoluble inorganic solid, acidic ion exchange resins, carbon treated with an inorganic acid, and mixtures thereof.

Preferably, the acidic insoluble inorganic solid is acidic aluminosilicates or silica gel.

Preferably, the inorganic acid, with which the carbon was treated, is selected from the group consisting of HCl, $H_2SO_4$ and $HNO_3$.

Preferably, the acidic ion exchange resin is selected from the group consisting of copolymers of styrene and divinylbenzene and of perfluorinated branched or linear polyethylenes, these polymers being functionalized with $SO_3H$ groups;

more preferably, the acidic ion exchange resin is selected from the group consisting of copolymers of styrene and divinylbenzene containing more than 5% of divinylbenzene, preferably being macroreticular, and of perfluorinated polyethylenes, these polymers being functionalized with $SO_3H$ groups.

When reaction (P-reac) is done in the presence of a catalyst (P-cat), temperature (P-temp) is preferably from 0 to 200° C., more preferably from 10 to 150° C., even more preferably from 10 to 100° C.

Reaction (P-reac) can be done in gas phase by passing evaporated compound of formula (XXIV) through a heated tube, the heated tube can be charged with a catalyst (P-cat).

After reaction (P-reac), the compound of formula (XXIII) can be isolated by standard methods such as evaporation of volatile components, extraction, washing, drying, concentration, crystallization, distillation, chromatography and any combination thereof.

Preferably, compound of formula (XXIV) is prepared in three steps, the three steps are a step (Q1), a step (Q2) and a step (Q3);

step (Q1) comprises a reaction (Q1-reac) by a reaction of compound of formula (XXV) with a reagent (Q1-reag);

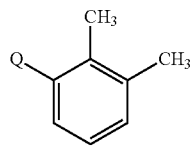

(XXV)

Q is Br, Cl, or I;

reagent (Q1-reag) is selected from the group consisting of lithium, magnesium, aluminum, zinc, calcium, isopropylmagnesium chloride, isopropylmagnesium bromide, butyllithium, sec-butyllithium and mixtures thereof;

step (Q2) comprises a reaction (Q2-reac);

reaction (Q2-reac) is a reaction of the reaction product of reaction (Q1-reac) with acetone;

in step (Q3) comprises a reaction (Q3-reac);

reaction (Q3-reac) is a reaction of the reaction product of reaction (Q2-reac) with a reagent (Q3-reag);

reagent (Q3-reag) is selected from the group consisting of water, methanol, ethanol, oxalic acid, citric acid, $NH_4Cl$, HCl, HBr, $HNO_3$, $H_2SO_4$, $H_3PO_4$, acetic acid, propionic acid, formic acid and mixtures thereof.

Preferably, Q is Br.

Preferably, reagent (Q1-reag) is selected from the group consisting of lithium, magnesium, aluminum, isopropylmagnesium chloride, isopropylmagnesium bromide and mixtures thereof.

Reaction (Q1-reac) can be catalyzed with a catalyst (Q1-cat).

Catalyst (Q1-cat) is selected from the group consisting of iodine, 1,2-dibromoethane, $TiCl_4$, $AlCl_3$, $PbCl_2$, $BiCl_3$, LiCl and mixtures thereof.

Preferably, reagent (Q3-reag) is water or aqueous $NH_4Cl$.

Preferably, reaction (Q1-reac) is performed in a solvent (Q1-solv).

Preferably, reaction (Q2-reac) is performed in a solvent (Q2-solv).

Preferably, reaction (Q3-reac) is performed in a solvent (Q3-solv).

Preferably, solvent (Q1-solv), solvent (Q2-solv) and solvent (Q3-solv) are identical or different and independently from each other selected from THF, methyl-THF, NMP, diethylether, methyl-tert-butylether, methoxycyclopentane, diisopropylether, 1,2-dimethoxyethane, tri $C_{1-4}$ alkyl amine and mixtures thereof;

more preferably from THF, 2-methyl-THF, 1,2-dimethoxyethane, methyl-tert-butylether, methoxycyclopentane, tri $C_{1-4}$ alkyl amine and mixtures thereof;

even more preferably from the group consisting of THF, 2-methyl-THF, 1,2-dimethoxyethane, triethylamine, and mixtures thereof.

Preferably the solvent (Q1-solv), solvent (Q2-solv) and solvent (Q3-solv) are identical.

The reaction temperatures of reaction (Q1-reac), of reaction (Q2-reac) and of reaction (Q3-reac) are identical or different and independently from each other preferably from −100 to 150° C., more preferably from −60 to 100° C., and even more preferably from −20 to 80° C.

Reaction (Q1-reac), reaction (Q2-reac) and reaction (Q3-reac) can be done at a constant temperature, or the temperature may be modified during the progress of the reactions. For instance, the reactions can run for a certain time at first temperature, and then for a subsequent time at a second temperature different from the first temperature. Alternatively, the temperature may be modified continuously during the reaction.

The reaction times of reaction (Q1-reac), of reaction (Q2-reac) and of reaction (Q3-reac) are identical or different and independently from each other preferably from 30 min to 48 h, more preferably from 1 to 24 h, even more preferably from 2 to 12 h.

The amounts of solvent (Q1-solv), of solvent (Q2-solv) and of solvent (Q3-solv) are identical or different and independently from each other preferably from 2 to 40 fold, more preferably from 3 to 10 fold, even more preferably from 5 to 7 fold, of the weight of compound of formula (XXV), of the weight of the reaction product of reaction (Q1-reac) and of the weight of the reaction product of reaction (Q2-reac) respectively.

Preferably, from 1.0 to 10 mol equivalents, more preferably from 1.1 to 5 mol equivalents, even more preferably from 1.1 to 3 mol equivalents of reagent (Q1-reag) are used, the mol equivalents being based on the mol of compound of formula (XXV).

Preferably, from 1.0 to 10 mol equivalents, more preferably from 1.1 to 5 mol equivalents, even more preferably from 1.1 to 3 mol equivalents of acetone are used, the mol equivalents being based on the mol of compound of formula (XXV).

Preferably, from 1.0 to 100 mol equivalents, more preferably from 1.1 to 50 mol equivalents, even more preferably from 1.1 to 30 mol equivalents of reagent (Q3-reag) are used, the mol equivalents being based on the mol of compound of formula (XXV) or of the mol of the reaction product of reaction (Q2-reac).

Preferably, reaction (Q1-reac), reaction (Q2-reac) and reaction (Q3-reac) are done at atmospheric pressure.

Preferably, reaction (Q1-reac), reaction (Q2-reac) and reaction (Q3-reac) are done under inert atmosphere. Preferably, the inert atmosphere is achieved by the use if an inert gas selected from the group consisting of argon, another noble gas, lower boiling alkane, nitrogen and mixtures thereof.

The lower boiling alkane is preferably a $C_{1-3}$ alkane, i.e. methane, ethane or propane.

After reaction (Q1-reac), reaction (Q2-reac) and reaction (Q3-reac), the reaction product of reaction (Q1-reac), the reaction product of reaction (Q2-reac) and compound of formula (XXIV) respectively can be isolated by standard methods such as evaporation of volatile components, extraction, washing, drying, concentration, crystallization, distillation, chromatography and any combination thereof.

Preferably, the reaction product of reaction (Q1-reac) and the reaction product of reaction (Q2-reac) are not isolated.

Preferably, reaction (Q1-reac), reaction (Q2-reac) and reaction (Q3-reac) are done consecutively; preferably, reaction (Q1-reac), reaction (Q2-reac) and reaction (Q3-reac) are done in one pot.

In another preferred embodiment, reaction (Q1-reac) and reaction (Q2-reac) can be done in one pot by adding reagent (Q1-reag) to a mixture of compound of formula (XXV) and acetone in a solvent (Q1-solv); reaction (Q3-reac) is done thereafter, preferably in the same pot.

Compound of formula (XXIV) is preferably isolated using conventional methods, such as evaporation of volatile components, hydrolysis and optional acidification of the higher-boiling residue, extraction, and distillation.

Any aqueous phase can be extracted, preferably the extraction is done with a solvent (Q-extract). Solvent (Q-extract) is benzene, toluene, ethyl acetate, or isopropyl acetate.

Any organic phase can be dried, preferably with magnesium sulphate.

Any concentration is preferably done by distillation, preferably under reduced pressure.

The compound of formula (XXIV) can be purified, preferably by crystallization or distillation under reduced pressure.

Compounds of formula (XXI) and (XXII) are chiral compounds, and the formulae comprise any enantiomer as well as any mixture of enantiomers of the compounds of formula (XXI), or of formula (XXII) respectively.

Compounds of formula (XXV) are known compounds and can be prepared according to known methods.

The progress of any of the reactions reaction (N-reac), reaction (O-reac), reaction (O1-reac), reaction (O2-reac), reaction (P-reac), reaction (Q1-reac), reaction (Q2-reac) and reaction (Q3-reac) can be monitored by standard techniques, such as nuclear magnetic resonance spectroscopy (NMR), infrared spectroscopy (IR), High performance Liquid Chromatography (HPLC), Liquid Chromatography Mass Spectrometry (LCMS), or Thin Layer Chromatography (TLC), and work-up of the reaction mixture can start, when the conversion of the starting material exceeds 95%, or when no more starting material can be detected. The time required for this to occur will depend on the precise reaction temperature and the precise concentrations of all reagents, and may vary from batch to batch.

In general, any organic phase can be dried, preferably over $MgSO_4$ or $Na_2SO_4$, if not stated otherwise.

Further subject of the invention is the use of compound of formula (XXI) as a fragrance, preferably in perfumes or house hold products.

Further subject of the invention is the use of compound of formula (XXI) for the preparation of medetomidine.

Medetomidine is compound of formula (XX)

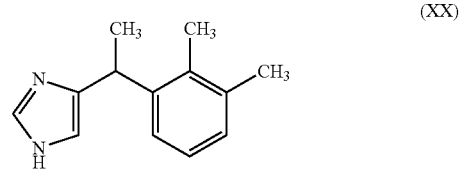

and is an alpha2 adrenergic agonist, which is currently being used as veterinary sedative and analgesic and is evaluated as anesthetic.

WO2011/070069A discloses a process for the preparation of medetomidine, in which the imidazole ring is built up during a multi-step process starting from commercially affordable 2,3-dimethyl benzoic acid.

Compound of formula (XX) is preferably prepared from compound of formula (XXI) by a method, that comprises a reaction (M1);

reaction (M1) is a reaction between a compound of formula (XXI), an isocyanide and a compound acting as nitrogen source;

the isocyanide is preferably a reagent (M), reagent (M) is selected from the group consisting of p-toluenesulfonylmethyl isocyanide, trifluoromethanesulfonylmethyl isocyanide, methanesulfonylmethyl isocyanide, benzenesulfonylmethyl isocyanide, 4-acetamidobenzenesulfonylmethyl isocyanide and mixtures thereof;

the compound acting as nitrogen source is preferably a reagent (M-A), reagent (M-A) is selected from the group consisting of ammonia, sulfamic acid, p-toluenesulfonamide, benzenesulfonamide, 4-acetamidobenzenesulfonamide, tritylamine, formamide, urea, urotropine, ethyl carbamate, acetamide and mixtures thereof;

preferably the reaction (M1) is done in a solvent (M), preferably solvent (M) is selected from the group consisting of N,N-dimethylformamide, $C_{1-6}$ alkanol, formamide, 1,2-dimethoxyethane, NMP, toluene, acetonitrile, propionitrile, ethyl carbamate, N,N-dimethylacetamide, water, acetamide and mixtures thereof.

Any sequence of the reaction of reagent (M) and of reagent (M-A) with the compound of formula (XXI) in reaction (M1) can be used:

compound of formula (XXI) can first be reacted with reagent (M) and then reagent (M-A) added;

or compound of formula (XXI) can first be first reacted with reagent (M-A) and then reagent (M) added;

or compound of formula (XXI) can simultaneously be reacted with reagent (M) and with reagent (M-A), this embodiment is preferably suited for the case that reagent (M-A) and solvent (M) are identical and are formamide, ethyl carbamate or acetamide; preferably formamide.

Further subject of the invention is the use of compound of formula (XXII) for the preparation of compound of formula (XXI).

Further subject of the invention is the use of compound of formula (XXIII) for the preparation of compound of formula (XXII).

Further subject of the invention is the use of compound of formula (XXIV) for the preparation of compound of formula (XXIII).

Further subject of the invention is the use of compound of formula (XXV) for the preparation of compound of formula (XXIV).

Compared to prior art, the method of the present invention offers several advantages:

Importantly, the whole carbon framework of compound of formula (XXI) is built in few chemical steps, using cheap reagents only. No protecting groups are needed and the overall amount of material used is therefore reduced, the batch size based on molar amounts is increased.

In particular no trityl or acetal protection groups are used and no protection of the imidazoles is necessary. Thereby the number and amount of reagents needed is reduced, and no protecting or deprotecting steps being needed the waste is reduced, contrary to when for example a trityl or acetal protecting group is used. The method has good yields.

Compound of formula (XXI) can be easily purified and obtained in a form of high odorous of fragrance purity or high fragrance purity. This is particularly important for products destined for use as fragrance.

The product is distinguished by a very special fragrance sought after in the fragrance industry.

EXAMPLES

Methods $^1H$ and $^{13}C$ NMR spectra were recorded on a Varian VNMRS 500 (500 MHz for $^1H$ and 125 MHz for $^{13}C$) instruments in $CDCl_3$. Chemical shifts are expressed in parts per million referred to TMS and coupling constants (J) in hertz.

EI means Electron ionization mass spectra (70 eV), they were obtained on an AMD-604 spectrometer.

ESI means Electron spray ionization mass spectra

THF was distilled from sodium/benzophenone ketyl prior to use; the obtained anhydrous THF is called "dry THF" in the following text.

Example 1

2-(2,3-Dimethylphenyl)propan-2-ol, compound of formula (XXIV), prepared via as organomagnesium intermediate 1-Bromo-2,3-dimethylbenzene (compound of formula (XXV), wherein Q is Br; 8.43 g, 45.6 mmol) was dissolved in dry THF (15 mL) and placed in dropping funnel. Separately, Mg wire (1.10 g, 45.3 mmol) in dry THF (5 mL) was placed in a flask equipped with the above mentioned dropping funnel, a stirrer, and a reflux condenser. The 1-bromo-2,3-dimethylbenzene solution (1.0 mL) was added via a dropping funnel and the reaction was initiated by the addition of 1,2-dibromoethane (3 drops), and then the rest of the 1-bromo-2,3-dimethylbenzene solution was added. The content of the dropping funnel was added at such a rate to maintain slight reflux. After completion of the addition, the mixture was refluxed for 1 h and then cooled to 0° C. A solution of dry acetone (4.2 mL, 58 mmol) in dry THF (15 mL) was added dropwise and the mixture was stirred at a temperature between 0 and 20° C. for 3 h. The mixture was poured into saturated $NH_4Cl$ aqueous solution (100 mL) extracted with hexane (5 times with 50 mL each), dried with $Na_2SO_4$ and evaporated under reduced pressure. The main product was isolated via silica gel column chromatography with hexane:ethyl acetate as eluent (v/v 15:1 to 10:1 gradient), to yield 3.50 g (47%) of the title compound.

$^1H$ NMR: 1.68 (s, 6H), 1.70 (s, 1H), 2.29 (s, 3H), 2.50 (s, 3H), 7.03 to 7.10 (m, 2H), 7.29 to 7.32 (m, 1H).

$^{13}C$ NMR: 17.72, 21.08, 31.24, 73.71, 123.11, 125.02, 129.02, 135.09, 138.69, 145.47. MS (EI): 164 (12), 149 (35), 146 (100), 131, 116, 105, 91.

Example 2

2-(2,3-Dimethylphenyl)propan-2-ol, compound of formula (XXIV), prepared via an organolithium intermediate 1-Bromo-2,3-dimethylbenzene (compound of formula (XXV), wherein Q is Br; 4.25 g, 23.0 mmol) was dissolved in dry THF (20 mL) in a flask equipped with a thermometer and a stirring bar. The mixture was cooled to −78° C. n-Butyllithium (1.6 M in hexane, 17.5 mL, 28.0 mmol) was added dropwise via a syringe, keeping the temperature below −70° C. When the addition was complete, the mixture was maintained at −78° C. and stirred at this temperature for 1 h. A solution of dry acetone (1.85 mL, 25.2 mmol) in dry THF (5 mL) was then added at −78° C. The mixture was stirred at −78° C. for 30 min, the cooling bath was removed, and the mixture was allowed to reach room temperature. The mixture was poured into saturated aqueous $NH_4Cl$ solution (100 mL), extracted with hexane (4 times with 50 mL each), dried over $Na_2SO_4$, and purified by via silica gel column chromatography using hexane:ethyl acetate as eluent (v/v 32:1) to give 3.45 g (91%) of the title compound. The measured NMR spectra were identical to those recorded in example 1.

Example 3

1,2-Dimethyl-3-(2-propenyl)benzene, compound of formula (XXIII)

2-(2,3-Dimethylphenyl)propan-2-ol, compound of formula (XXIV), prepared according to either example 1 or example 2, (1.10 g, 6.70 mmol), was dissolved in benzene (20 mL), and p-toluenesulfonic acid monohydrate (35 mg, 0.18 mmol) was added. The mixture was stirred at room temperature for 3 h. Silica gel (200 mg) was added, and stirring was continued for ca. 16 hours, and then the reaction mixture was refluxed for 30 min. After cooling to room temperature, the mixture was filtered, washed with aqueous $K_2CO_3$ solution, conventionally dried, and concentrated under reduced pressure, to yield 0.90 g (92%) of the title compound.

$^1$H NMR: 2.02 (m, 3H), 2.21 (s, 3H), 2.28 (s, 3H), 4.82 (m, 1H), 5.17 (m, 1H), 6.97 (m, 1H), 7.05 (m, 2H).

Example 4

2-(2,3-Dimethylphenyl)methyloxirane, compound of formula (XXII)

A buffer was prepared by dissolving $K_2CO_3$ (20.7 g) and EDTA-$Na_2$ (11.5 mg) in water (100 mL). 1,2-Dimethyl-3-(2-propenyl)benzene, compound of formula (XXIII), prepared according to example 3 (0.90 g, 6.16 mmol), was dissolved in a mixture of dichloromethane and acetonitrile (v/v 1:1, 60 mL), and the buffer prepared as described above (9.3 mL) was added. To the resulting mixture, first 1,1,1-trifluoroacetone (60 µL) and then hydrogen peroxide (30% in water, 6.2 mL, 60.7 mmol) were added and the mixture was stirred at room temperature for 2 h. The reaction mixture was diluted with water (100 mL), the organic phase was separated, and the aqueous phase was extracted with dichloromethane (2 times with 50 mL each). The combined organic phases were dried over $Na_2SO_4$, concentrated under reduced pressure, and the residue was purified by via silica gel column chromatography using hexane:ethyl acetate as eluent (v/v 32:1) to give 851 mg (85%) of the title compound.

$^1$H NMR: 1.59 (s, 3H), 2.28 (s, 3H), 2.31 (s, 3H), 2.83 (br d, J=5.4, 1H), 2.98 (d, J=5.4 Hz, 1H), 7.08 (m, 2H), 7.21 (m, 1H).

MS (EI): 162, 147, 133, 117 (100).

Example 5

2-(2,3-Dimethylphenyl)propanal, compound of formula (XXI)

2-(2,3-Dimethylphenyl)methyloxirane, compound of formula (XXII), prepared according to example 4 (0.84 g, 5.18 mmol), was dissolved in dry dichloromethane (50 mL) and powdered Cu(BF$_4$)$_2$ hydrate (318 mg) was added at room temperature. After 2 h at room temperature, the mixture was washed with water, dried over $Na_2SO_4$ and concentrated under reduced pressure to yield 0.84 g (100%) of the title product.

$^1$H NMR: 1.40 (d, J=7.1 Hz, 3H), 2.25 (s, 3H), 2.32 (s, 3H), 3.89 (qd, J=7.1, 1.0 Hz, 1H), 6.89 to 6.92 (m, 1H), 7.12 (m, 2H), 9.67 (d, J=1.0 Hz, 1H).

Example 6

Medetomidine, compound of formula (XX)

2-(2,3-Dimethylphenyl)propanal, compound of formula (XXI), prepared according to example 5 (2.43 g, 15.0 mmol) and p-toluenesulfonylmethyl isocyanide (2.73 g, 14.0 mmol) were mixed with EtOH (30 mL). To the stirred suspension powdered NaCN (73 mg, 1.5 mmol) was added. The mixture was stirred for 1 h at room temperature, and then evaporated under reduced pressure to dryness. The residue was placed in an ampoule and treated with MeOH saturated with $NH_3$ (50 mL). The ampoule was heated to 110° C. in an oil bath for three days.

This experiment was repeated once more (2-(2,3-Dimethylphenyl)propanal: 3.24 g, 20.0 mmol; p-toluenesulfonylmethyl isocyanide: 3.90 g, 20.0 mmol).

Both reaction mixtures were combined, evaporated to dryness, dissolved in dichloromethane (150 mL) and washed with 10% (w/w) aqueous $Na_2CO_3$ (200 mL) and then with water (200 mL), conventionally dried, evaporated under reduced pressure and purified by via silica gel column chromatography using dichloromethane:methanol as eluent (v/v 15:1 to 10:1 gradient), to yield 3.0 g (44%) of medetomidine as a sticky oil. Medetomidine was crystallized from toluene:cyclohexane, and then recrystallized from aqueous ethanol.

$^1$H NMR: 1.56 (d, J=7.2 Hz, 3H), 2.18 (s, 3H), 2.25 (s, 3H), 4.35 (q, J=7.2 Hz, 1H), 6.66 (s, 1H), 6.93 (dd, J=6.6, 2.2 Hz, 1H), 6.99 to 7.05 (m, 2H), 7.30 (d, J=1.1 Hz, 1H), 9.84 (broad s, 1H).

$^{13}$C NMR: 14.65, 20.72, 20.88, 14.12, 117.61, 124.62, 125.53, 127.91, 134.05, 134.60, 136.76, 141.11, 143.23.

MS (ESI): 201 [M+H]$^+$

The invention claimed is:

1. A method for the preparation of a compound of formula (XXI),

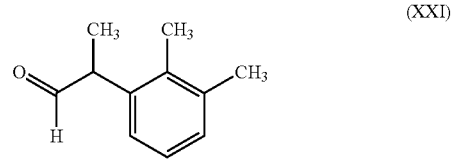

the method comprises a step (N);
step (N) comprises a reaction (N-reac);
reaction (N-reac) is a reaction of a compound of formula (XXII) with a catalyst (N-cat);

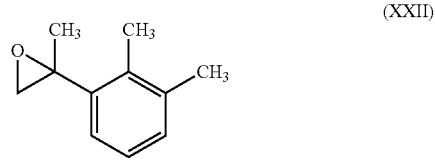

catalyst (N-cat) is selected from the group consisting of acetic acid, formic acid, trifluoroacetic acid, methanesulfonic acid, benzenesulfonic acid, p-toluenesulfonic acid, camphorsulfonic acid, HCl, HBr, $H_2SO_4$, $HNO_3$, $H_3PO_4$, $HClO_4$, $BCl_3$, $BBr_3$, $BF_3OEt_2$, $BF_3SMe_2$, $BF_3THF$, $MgCl_2$, $MgBr_2$, $MgI_2$, $AlCl_3$, $Al(O-C_{1-4}$ alkyl$)_3$, $SnCl_4$, $TiCl_4$, $Ti(O-C_{1-4}$ alkyl$)_4$, $ZrCl_4$, $Bi_2O_3$, $BiCl_3$, $ZnCl_2$, $PbCl_2$, $FeCl_3$, $ScCl_3$, $NiCl_2$, $Yb(OTf)_3$, $Yb(Cl)_3$, $GaCl_3$, $AlBr_3$, $Ce(OTf)_3$, $LiCl$, $Cu(BF_4)_2$, $Cu(OTf)_2$, $NiBr_2(PPh_3)_2$, $NiBr_2$, $NiCl_2$, $Pd(OAc)_2$, $PdCl_2$, $PtCl_2$, $InCl_3$, acidic inorganic solid substance, acidic ion exchange resin, carbon treated with inorganic acid and mixtures thereof.

2. The method according to claim 1, wherein the catalyst (N-cat) is selected from the group consisting of acetic acid, formic acid, trifluoroacetic acid, methanesulfonic acid, p-toluenesulfonic acid, HCl, HBr, $H_2SO_4$, $H_3PO_4$, $BCl_3$, $BF_3OEt_2$, $MgCl_2$, $MgBr_2$, $AlCl_3$, $ZnCl_2$, $Cu(BF_4)_2$, aluminosilicates, acidic ion exchange resins, carbon treated with HCl, $H_2SO_4$ or $HNO_3$, and mixtures thereof.

3. The method according to claim 1, wherein reaction (N-reac) is done in a solvent (N-solv);
solvent (N-solv) is selected from the group consisting of water, tert-butanol, isopropanol, acetonitrile, propionitrile, THF, methyl-THF, NMP, dioxane, 1,2-dimethoxyethane, dichloromethane, 1,2-dichloroethane, chloroform, toluene, benzene, chlorobenzene, hexane, cyclohexane, ethyl acetate, acetic acid, formic acid, trifluoroacetic acid and mixtures thereof.

4. The method according to claim 1, wherein the compound of formula (XXII) is prepared in a step (O) or in two steps, wherein the two steps are a step (O1) and a step (O2);
step (O) comprises a reaction (O-reac);
reaction (O-reac) is a reaction of a compound of formula (XXIII), with a reagent (O-reag);

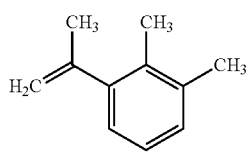

(XXIII)

reagent (O-reag) is selected from the group consisting of peracetic acid, trifluoroperacetic acid, perbenzoic acid, 3-chloroperbenzoic acid, monoperphthalic acid, dimethyldioxirane, tert-butylhydroperoxide, dibenzoyl peroxide, cumenehydroperoxide, oxygen, air, sodium hypochlorite, $KHSO_5$, $Na_2O_2$, aqueous $H_2O_2$, $H_2O_2$ dissolved in acetic acid, $H_2O_2$ dissolved in trifluoroacetic acid, and mixtures thereof;
step (O1) comprises a reaction (O1-reac);
reaction (O1-reac) is a reaction of a compound of formula (XXIII) with water and with a compound (O1-comp) to provide a reaction product from reaction (O1-reac);
compound (O1-comp) is selected from the group consisting of bromine, N-bromosuccinimide, chlorine, N-chlorosuccinimide, iodine, N-iodosuccinimide, IBr, BrCl, and mixtures thereof;
step (O2) comprises a reaction (O2-reac);
reaction (O2-reac) is a reaction of the reaction product from reaction (O1-reac) with a base (O2-base);
base (O2-base) is selected from the group consisting of sodium hydroxide, potassium hydroxide, calcium hydroxide and mixture thereof.

5. The method according to claim 4, wherein reagent (O-reag) is selected from the group consisting of peracetic acid, tert-butylhydroperoxide, oxygen, air, sodium hypochlorite, aqueous $H_2O_2$, $H_2O_2$ dissolved in acetic acid, $H_2O_2$ dissolved in trifluoroacetic acid, and mixtures thereof.

6. The method according to claim 4, wherein the compound of formula (XXIII) is prepared in a step (P);

step (P) comprises a reaction (P-reac);
in reaction (P-reac) a compound of formula (XXIV) is exposed to a temperature (P-temp);

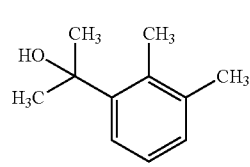

(XXIV)

temperature (P-temp) is from 0 to 300° C.

7. The method according to claim 6, wherein the compound of formula (XXIV) is prepared in three steps, the three steps are a step (Q1), a step (Q2) and a step (Q3);
step (Q1) comprises a reaction (Q1-reac) by a reaction of a compound of formula (XXV) with a reagent (Q1-reag) to provide a reaction product of reaction (Q1-reac);

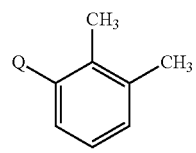

(XXV)

Q is Br, Cl, or I;
reagent (Q1-reag) is selected from the group consisting of lithium, magnesium, aluminum, zinc, calcium, isopropylmagnesium chloride, isopropylmagnesium bromide, butyllithium, sec-butyllithium and mixtures thereof;
step (Q2) comprises a reaction (Q2-reac);
reaction (Q2-reac) is a reaction of the reaction product of reaction (Q1-reac) with acetone to provide a reaction product of reaction (Q2-reac);
step (Q3) comprises a reaction (Q3-reac);
reaction (Q3-reac) is a reaction of the reaction product of reaction (Q2-reac) with a reagent (Q3-reag);
reagent (Q3-reag) is selected from the group consisting of water, methanol, ethanol, oxalic acid, citric acid, $NH_4Cl$, HCl, HBr, $HNO_3$, $H_2SO_4$, $H_3PO_4$, acetic acid, propionic acid, formic acid and mixtures thereof.

8. A fragrance comprising the compound of formula (XXI) as defined in claim 1.

9. A method for the preparation of medetomidine, the method comprising reacting the compound of formula (XXI) as defined in claim 1, an isocyanide, and a nitrogen compound selected from the group consisting of ammonia, sulfamic acid, p-toluenesulfonamide, benzene sulfonamide, 4-acetamidobenzenesulfonamide, tritylamine, formamide, urea, urotropine, ethyl carbamate, acetamide and mixtures thereof.

* * * * *